United States Patent [19]

Tsuji et al.

[11] Patent Number: 4,895,956

[45] Date of Patent: Jan. 23, 1990

[54] 3-AROYL-6,7-DIHYDRO-5H-PYRROLO(1,2-C)IMIDAZOLE-7-CARBOXYLIC ACID DERIVATIVES

[75] Inventors: Masayoshi Tsuji, Tosu; Hisataka Inoue, Kurume; Yoshihiro Tanoue, Fukuoka; Kouichi Beppu, Tosu; Masaru Saita, Saga; Yasuaki Taniguchi, Tosu; Kenichi Furuta, Chikushino; Yoshiki Deguchi, Tosu; Kanji Noda, Chikushino, all of Japan

[73] Assignee: Hisamitsu Pharmaceutical Co., Ltd., Tosu, Japan

[21] Appl. No.: 242,331

[22] Filed: Sep. 8, 1988

[30] Foreign Application Priority Data

Sep. 10, 1987 [JP] Japan ................................. 62-227702

[51] Int. Cl.$^4$ ............................................. C07D 487/04
[52] U.S. Cl. ................................... 548/324; 546/168; 546/271; 548/181; 548/235
[58] Field of Search ....................... 548/324, 181, 235; 546/168, 271

[56] References Cited

U.S. PATENT DOCUMENTS 4,347,185 8/1982 Muchowski et al. ........... 544/275 X

FOREIGN PATENT DOCUMENTS 011417 5/1980 European Pat. Off. .
096583 12/1983 European Pat. Off. .
096816 12/1983 European Pat. Off. .
2731678 3/1978 Fed. Rep. of Germany .

OTHER PUBLICATIONS

*Chemical Abstracts,* 71:3201t(1969) [Kogan et al., Khim.-Farm. 2H., 1969, 3(2), 12–14].
*Chemical Abstracts,* 89:6215h(1978) [Ger. Offem, 2,731,678, Muchowski et al., 3/16/78].

*Primary Examiner*—Richard A. Schwartz
*Attorney, Agent, or Firm*—Bucknam and Archer

[57] ABSTRACT

A novel 3-aroyl-6,7-dihydro-5H-pyrrolo[1,2-c]imidazole-7-carboxylic acid derivative which is useful as a medicine having excellent analgesic and anti-inflammatory actions with remarkably less toxicity and side-effects.

1 Claim, No Drawings

3-AROYL-6,7-DIHYDRO-5H-PYRROLO(1,2-C)IMIDAZOLE-7-CARBOXYLIC ACID DERIVATIVES

BACKGROUND OF THE INVENTION

1. Field of the Invention

This invention relates to the field of compounds useful as non-steroid type antiphlogistic agents which have excellent anti-inflammatory and analgesic actions and less side-effects and more specifically to novel 3-aroyl-6,7-dihydro-5H-pyrrolo[1,2-c]imidazole-7-carboxylic acid derivatives.

2. Prior Art

Many of 6,7-dihydro-5H-pyrrolo[1,2-c]imidazole derivatives which have heretofore been proposed, are those which are not substituted at the 3-position, while some other derivatives are those wherein only a phenyl group has been introduced to such a position (Khim.-Farm. Zh., 1969, 3(2), 12–14; CA 71 (1): 3201t (1969), etc.); however, none of such derivatives that have an aroyl group at the 3-position have ever been disclosed. In addition, such drivatives that have a carboxylic group at the 7-position have never been reported either. Thus, the 3-aroyl-6,7-dihydro-5H-pyrrolo[1,2-c]imidazole-7-carboxylic acids of the present invention are quite unknown although 5-aroyl-1,2-dihydro-3H-pyrrolo[1,2-a]pyrrole-1-carboxylic acid derivatives having a structure similar to that of the derivatives of the present invention have been reported in Ger. Offen. 2731678, etc.

SUMMARY OF THE INVENTION

The primary object of the present invention is to provide a novel 3-aroyl-6,7-dihydro-5H-pyrrolo[1,2-c]imidazole-7-carboxylic acid derivative for use as a medicine which when used will not only exhibit excellent analgesic and anti-inflammatory actions, but also exhibit remarkably low toxicity and remarkably small side-effects (for example, slight gastric mucous membrane disturbances) as compared with conventional anti-inflammatory and analgesic drugs.

The present invention resides in a 3-aroyl-6,7-dihydro-5H-pyrrolo[1,2-c]imidazole-7-carboxylic acid derivative represented by the following formula

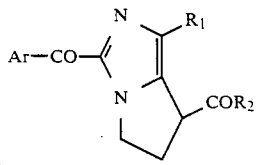

[I]

wherein $R_1$ is a hydrogen atom, halogen atom, trihalomethyl group, alkyl group, alkoxy group, alkylthio group, alkylsulfinyl group or alkylsulfonyl group; Ar is a non-substituted or substituted phenyl group, or a non-substituted or substituted heterocyclic group; and $R_2$ is hydroxyl group, an ester residue or amino group.

The formula (I) will be more concretely explained below.

In the formula, Ar is a non-substituted phenyl group or a substituted phenyl group having 1 to 5 substituents which are identical with, or different from, each other. The substituents include a halogen atom, trihalomethyl group, alkyl group, alkoxy group, alkylthio group, alkylsulfinyl group, alkylsulfonyl group, nitro group and amino group.

The halogen atom in $R_1$ and Ar includes fluorine, chlorine, bromine or iodine. The trihalomethyl group includes trifluoromethyl group. The alkyl group includes a straight- or branched-chain alkyl group having 1 to 20 carbon atoms and is illustrated by methyl, ethyl, propyl, butyl, pentyl, hexyl, heptyl, octyl, nonyl, decyl, pentadecyl, eicosyl, isopropyl, isobutyl, tertiarybutyl, isopentyl, neopentyl or isohexyl group. The alkoxy group includes a straight- or branched-chain one and is illustrated by methoxy, ethoxy, propoxy, butoxy, isopropoxy, isobutoxy or tertiarybutoxy group. The alkylthio group includes a straight- or branched-chain one and is illustrated by methylthio, ethylthio, propylthio, butylthio, isopropylthio, isobutylthio or tertiarybutylthio group. The alkylsulfinyl group includes a straight- or branched-chain one and is illustrated by methylsulfinyl, ethylsulfinyl, propylsulfinyl, butylsulfinyl, isopropylsulfinyl, isobutylsulfinyl or tertiarybutylsulfinyl group. The alkylsulfonyl group includes a straight- or branched-chain one and is illustrated by methylsulfonyl, ethylsulfonyl, propylsulfonyl, butylsulfonyl, isopropylsulfonyl, isobutylsulfonyl or tertiarybutylsulfonyl group. The group Ar includes naphthyl or an heterocyclic such as 2-thienyl, 3-thienyl, 2-furyl, 3-furyl, 2-pyridyl, 3-pyridyl, 4-pyridyl, N-methyl-2-pyrrolyl, N-methyl-3-pyrrolyl, 2-imidazolyl, 4-imidazolyl, 2-thiazolyl, 4-thiazolyl, 5-thiazolyl, 2-oxazolyl, 4-oxazolyl, 5-oxazolyl, 3-pyrazolyl, 4-pyrazolyl or quinolyl group.

The ester residue in $R_2$ is among the following four ones:

(1) —OY wherein Y is an alkyl group, phenyl or a substituted phenyl group, or a heterocyclic or substituted heterocyclic group;

(2) —O(CH$_2$)$_m$—OH wherein m is an integer of 1 to 7;

(3) —O(CH$_2$)$_m$ COOW wherein m is an integer of 1 to 7 and W is a hydrogen atom or alkyl group; and (4) —O(CH$_2$)$_m$—Z wherein m is an integer of 1 to 7 and Z is phenyl or a substituted phenyl group or a heterocyclic or substituted heterocyclic group.

The alkyl group in said Y and W includes a straight- or branched-chain alkyl group having 1 to 20 carbon atoms and is illustrated by methyl, ethyl, propyl, butyl, pentyl, hexyl, isopropyl, isobutyl, tertiarybutyl, isopentyl, isohexyl, geranyl or farnesyl group. The substituted phenyl group and substituted heterocyclic group in said Y and Z are those wherein 1 to 5 substituents have been attached to the optional position or positions, the substituents including a halogen atom, trihalomethyl group, alkyl group, alkoxy group, alkylthio group, alkylsulfinyl group, alkylsulfonyl group, nitro group and amino group (The more specifically named substituents in said $R_1$ and Ar apply to the substituents in said Y and Z, and the more specifically named heterocyclic groups in said Ar apply to the heterocyclic groups in said Y and W). The ester residue (1), that is —OY, includes an alkoxy group such as methoxy, ethoxy, propoxy, butoxy, pentoxy, isopropoxy, isobutoxy, tertiarybutoxy, geranyloxy or farnesyloxy group and also includes phenoxy, 4-chlorophenoxy, anisyloxy, 4-methylthiophenoxy, 2-fluorophenoxy, 4-nitrophenoxy, 2,4-dichlorophenoxy, 4-isopropylphenoxy, 2-pyridyloxy, 3-pyridyloxy, 4-pyridyloxy, biphenyloxy or naphthyloxy group. The ester residue (2), that is —O(CH$_2$)$_m$—OH, includes 2-hydroxyethoxy group, 3-hydroxypropoxy or 4-hydroxybutoxy group. The ester residue (3), that is —O(CH$_2$)$_m$ COOW, includes carboxymethyloxy, ethoxycarbonylmethyloxy, 2-carboxyethyloxy, 3-carboxypropyloxy or 4-carboxybutyloxy group. The ester residue (4), that is —O(CH$_2$)$_m$—Z, includes benzyloxy, 4-fluorobenzyloxy, 4-methoxybenzyloxy, 2,4-dichlorobenzyloxy, 2-phenylethoxy, 3-phenylpropoxy, 2-pyridylmethyloxy, 3-pyridylmethyloxy, 4-pyridylmethyloxy, furfuryloxy or 2-thienylethyloxy group.

The amino group included in said R$_2$ includes an alkylamino group such as methylamino, ethylamino, propylamino, butylamino, isopropylamino group; a substituted alkylamino group such as a —NH—(CH$_2$)$_n$—R$_3$ group (wherein n is an integer of 0 to 6 and R$_3$ is an alkoxy group, alkylamino group or a cycloamino group such as piperidino, pyrrolidino, morpholino, piperazino, pipecolino or lupetidino group); a disubstituted amino group such as dimethylamino, diethylamino, dipropylamino or dibutylamino group; a cycloalkylamino group such as cyclobutylamino, cyclopentylamino or cyclohexylamino group; aniline or a phenylamino group containing a halogen atom, alkyl group, alkoxy group, nitro group or hydroxyl group as a substituent; a heterocycloamino group such as 2-pyridylamino, 2-(2-thiazoline)amino, 2-(3-methylthiazolone)imino, thienylamino, oxazolylamino, isoxazolylamino, furylamino or pyrrolylamino group; a cycloamino group such as morpholino, piperidino, pyrrolidino piperazino, pipecolino or lupetidino group; an amino acid such as glycine, leucine, alanine, serine or valine; or an amino acid alkyl ester.

The compounds of the present invention my be incorporated with a conventional vehicle to be shaped into pharmaceutically acceptable medicinal forms. They may be in the form of tablets, granules, sirups, capsules or the like for use as an oral medicine or in the form of an injection, suppository, ointment, gel, cream, lotion, liniment or plaster for use as a non-oral medicine. If necessary, the compounds of the present invention may be reacted with an inorganic salt (such as a sodium salt, potassium salt, calcium salt, hydrochloride, aluminum salt or the like) or with an organic salt (such as a fumarate, maleate, succinate, phthalate or lysine salt) to produce an addition salt. Further, they may be incorporated with cyclodextrin or the like to produce an inclusion compound in order to improve themselves in stability and solubility.

A process for preparing the compounds of the present invention will be illustrated hereunder. These compounds may be obtained in a good yield by the following exemplary process:

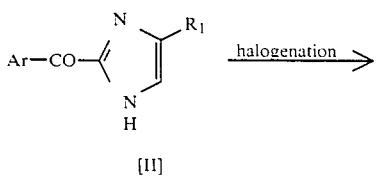

[II]

halogenation →

-continued

[III] → [IV]

[V] ring breakage →

[VI] ring closure →

[VII] hydrolysis decarbonation →

[I']

[I''] dehalogenation →

-continued

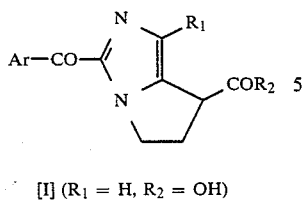

[I] ($R_1$ = H, $R_2$ = OH)

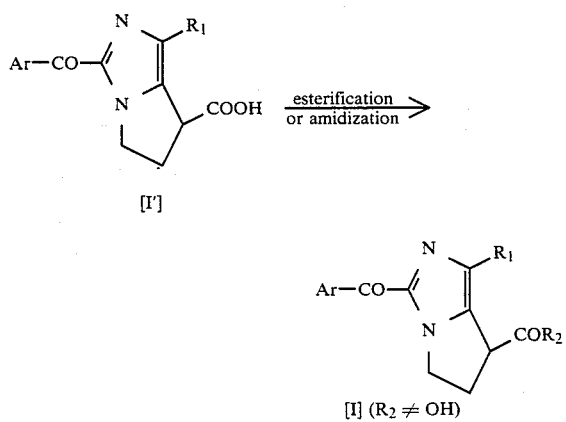

In the above process, Ar, $R_1$ and $R_2$ are as defined above, X is a halogen atom such as chlorine or bromine atom, and R is methyl or ethyl group.

The above process will be detailed hereunder.

A compound (II) obtained by a process described in, for example, SYNTHESIS, 9, 675(1978) is treated with a halogenating agent (such as bromine or sodium hypochlorite) to obtain a halogeno compound (III) which is reacted with a cyclopropane derivative(IV) in an inert solvent (such as dimethylformamide, tetrahydrofuran or benzene) in the presence of a base (such as sodium hydride, potassium tert.-butoxide or potassium carbonate) thereby to obtain a compound (V). The said cyclopropane derivative (IV) may be produced by a process described in ORGANIC SYNTHESIS, 60, 66–71(1981). The compound (V) so obtained is reacted with methanol or methanol containing hydrogen chloride to obtain a compound (VI) which is then subjected to a ring closure reaction in an inert solvent (such as dimethylformamide, tetrahydrofuran or benzene) in the presence of a base (such as sodium hydride, potassium tertiarybutoxide or potassium carbonate) thereby to obtain a compound (VII). The compound (VII) so obtained is subjected to hydrolysis in the presence of an inorganic base (such as potassium carbonate, sodium hydroxide or potassium hydroxide) whereby decarbonation is easily caused to produce a compound (I'); further, in the case of $R_1 = X$ [compound (I'')], the compound (I'') is subjected to catalytic reduction in the presence of palladium carbon etc. thereby obtaining a compound (I) ($R_1 = H$, $R_2 = OH$) wherein no substitution is caused at the 1-position. In addition, a carboxyl group at the 7-position may be converted to various esters nd amides according to a conventional method which is known to those in the art. The compound (VII) ($R_1 = X$) may be converted to various 1-alkylthio type compounds by a halogenmetal exchange reaction using a strong base such as butyllithium, and the 1-alkylthio group may further be converted to an alkylsulfinyl or alkylsulfonyl group depending on the degree of oxidation thereof, after which a desired product can be obtained through a series of hydrolyzing and decarbonating reactions.

DESCRIPTION OF THE PREFERRED EMBODIMENTS

The present invention will be better understood by the following non-limitative Examples wherein all percentages are by weight unless otherwise specified.

EXAMPLE 1

Twenty-three grams (23 g) of 2-benzoylimidazole were suspended in about 150 ml of water containing 11 g of sodium hydroxide, after which the whole was incorporated dropwise with 43 g of bromine under agitation at 20°–25° C. and, after completion of the dropwise incorporation, was agitated at the same temperature for additional one hour and then filtered off to collect the resulting crystals. The thus collected crystals were washed with water to the extent that the washings exhibit approximately neutrality, thereafter air-dried and then recrystallized from 300 ml of ethanol thereby to obtain 29.2 g of 2-benzoyl-4,5-dibromoimidazole. The thus obtained compound had the following melting point and elemental analysis:

Melting point: 215°–217° C.; Elemental analysis $C_{10}H_6N_2OBr_2$; Theoretical: C: 36.40, H: 1.83, N: 8.49; Found: C: 36.61, H: 2.04, N: 8.32.

EXAMPLE 2

Twenty-three point six grams (23.6 g) of 2-benzoyl-4,5-dibromoimidazole were dissolved in 200 ml of dimethylformamide, thereafter ice-cooled and then incorporated portionwise with 3.3 g of 60% sodium hydride under agitation in a nitrogen stream. The whole was further agitated at room temperature for 30 minutes, incorporated at one time with 15 g of 6,6-dimethyl 5,7-dioxaspiro[2,5]octane 4,8-dione and then reacted at 80°–90° C. for two hours. After cooled, the reaction mixture was added to 600 ml of ice water, made weakly acidic with concentrated hydrochloric acid, extracted twice with 400 ml of ethyl acetate and then water washed. The organic layer obtained was dehydrated and then concentrated under a reduced pressure to obtain a residue which was refined by silica gel column chromatography using a 1:1 ethyl acetate/hexane mixed liquid as the developed solvent, thereby to obtain 27 g of an oily compound (V) (Ar=$C_6H_5$, $R_1 = X = Br$). The thus obtained compound was further refined under the same conditions as above. The elemental analysis of the final product was as follows:

Elemental analysis: $C_{18}H_{16}N_2O_5Br_2$; Theoretical: C: 43.23, H: 3.22, N: 5.60; Found: C: 43.50, H: 3.15, N: 5.81.

EXAMPLE 3

Twenty (20) grams of the compound (V) (Ar=$C_6H_5$, $R_1 = X = Br$) were incorporated with 40 ml of a 15% HCl/EtOH solution and refluxed under heat for 30 minutes. After the end of the reaction, the reaction mixture was concentrated by removing the solvent under a reduced pressure, incorporated with about 50 ml of iced water, extracted twice with 50 ml of ethyl acetate and then washed with water. The organic layer obtained was dehydrated and concentrated under a reduced pressure to obtain a residue which was then refined by silica gel column chromatography using a 1:1 isopropyl ether/hexane mixed liquid as the developing solvent, thereby to obtain 12.8 g of an oily compound (VI) (Ar=$C_6H_5$, $R_1$=X=Br, R=$C_2H_5$).

The compound so obtained had the following elemental analysis:

Elemental analysis: $C_{19}H_{20}N_2O_5Br_2$; Theoretical: C: 44.21, H: 3.91, N: 5.43; Found: C: 44.43, H: 3.80, N: 5.41.

EXAMPLE 4

Ten (10) grams of the compound (VI) (Ar=$C_6H_5$, $R_1$=X=Br, R=$C_2H_5$) were dissolved in 30 ml of dimethylformamide, ice-cooled and then incorporated in portions with 0.8 g of 60% sodium hydride under agitation in a nitrogen stream. The whole was agitated at room temperature for about 30 minutes and heated to 80°–90° C. for 10 minutes. After cooled, the reaction mixture was added to about 100 ml of iced water, made weakly acidic with conc. hydrochloric acid, extracted twice with 80 ml of ethyl acetate and water washed. The organic layer obtained was dehydrated and concentrated under a reduced pressure to obtain a residue which was then refined by silica gel column chromatography using a 1:1 isopropyl ether/hexane mixed liquid as the developing solvent, thereby to obtain 6.7 g of an oily compound (VII) (Ar=$C_6H_5$, $R_1$=Br, R=$C_2H_5$). The compound so obtained had the following elemental analysis:

Elemental analysis: $C_{19}H_{19}N_2O_5Br$; Theoretical: C: 52.43, H: 4.40, N: 6.44; Found: C: 52.32, H: 4.29, N: 6.63.

EXAMPLE 5

Six point five (6.5) grams of the compound (VII) (Ar=$C_6H_5$, $R_1$=Br, R=$C_2H_5$) were incorporated with 30 ml of aqueous methanol containing 1.7 g of sodium hydroxide and refluxed under heat for about 10 minutes. After the end of the reaction, the reaction mixture was concentrated by removing the solvent under a reduced pressure, incorporated with 50 ml of iced water, washed with 30 ml of ethyl acetate, after which the aqueous layer was made weakly acidic with conc. hydrochloric acid to precipitate crystals which were filtered off. The rough crystals obtained were water washed, air-dried and then recrystallized from ethyl acetate thereby to obtain 4.1 g of 3-benzoyl-1-bromo-6,7-dihydro-5H-pyrrolo[1,2-c]imidazole-7-carboxylic acid.

The thus obtained compound had the following melting point and elemental analysis:

Melting point: 190°–192° C.; Elemental analysis: $C_{14}H_{11}N_2O_3Br$; Theoretical: C: 50.17, H: 3.31, N: 8.36; Found: C: 50.31, H: 3.19, N: 8.47.

EXAMPLE 6

Three (3) grams of 3-benzoyl-1-bromo-6,7-dihydro-5H-pyrrolo[1,2-c]imidazole-7-carboxylic acid were dissolved in 200 ml of a 50% water/methanol mixed liquid, containing 0.7 g of sodium hydroxide incorporated with 1.5 g of magnesium oxide and 0.6 g of 5% palladium/carbon and then agitated to the extent that absorption of the hydrogen gas is stopped (about 4 hours). After the end of the reaction, the reaction mixture was filtered and washed several times with water and methanol. The filtrate was concentrated under a reduced pressure and washed twice with about 70 ml of ethyl acetate. The aqueous layer obtained was made weakly acidic with conc. hydrochloric acid to precipitate crystals which were then filtered off. The rough crystals obtained were water washed, air-dried and then recrystallized from ethanol to obtain 2.1 g of 3-benzoyl-6,7-dihydro-5H-pyrrolo[1,2-c]imidazole-7-carboxylic acid.

The thus obtained compound had the following melting poing and elemental analysis:

Melting point: 232°–233° C.;

Elemental analysis: $C_{14}H_{12}N_2O_3$; Theoretical: C: 65.62, H: 4.72, N: 10.93; Found: C: 65.49, H: 4.83, N: 11.04.

EXAMPLE 7

One gram of 3-benzoyl-6,7-dihydro-5H-pyrrolo[1,2-c]imidazole-7-carboxylic acid, 0.8 g of dicyclohexylcarbodiimide and 0.6 g of p-nitrophenol were added to 50 ml of chloroform and then agitated at room temperature for one hour. The crystals precipitated were filtered off and the filtrate was incorporated with 1 g of glycine ethyl ester hydrochloride and 0.8 g of triethylamine and then agitated at room temperature for 15 hours. After the end of the reaction, the reaction mixture was washed with a 1-N ammonia water to the extent that the mixture became approximately colorless and further washed with a 1-N hydrochloric acid and with water, after which the chloroform layer was dehydrated and concentrated under a reduced pressure to obtain a residue which was refined by silica gel column chromatography. Using ethyl acetate as the developing solvent, 0.95 g of a compound (I) (Ar=$C_6H_5$, $R_1$=H, $R_2$=$NHCH_2CO_2C_2H_5$) were obtained from the main fraction. The compound so obtained was added to 20 ml of aqueous methanol containing 0.33 g of sodium hydroxide and then refluxed under heat for 10 minutes. After the end of the reaction, the reaction mixture was concentrated by distilling off the solvent at a reduced pressure to obtain a residue which was made weakly acidic with 10% hydrochloric acid thus precipitating crystals and filtering them off. The rough crystals so filtered off were water washed, air-dried and then recrystallized from ethanol to obtain 0.7 g of a compound (I) (Ar=$C_6H_5$, $R_1$=H, $R_2$=$NHCH_2COOH$).

The compound so obtained had the following melting point and elemental analysis:

Melting point: 247°–249° C.;

Elemental analysis: $C_{16}H_{15}N_3O_4$; Theoretical: C: 61.34, H: 4.83, N: 13.41, Found: C: 61.57, H: 4.92, N: 13.28.

EXAMPLES 8–25

The following final compounds were synthesized in accordance with the methods used in Examples 1 to 7.

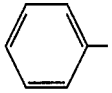
| Example No. | Ar | R₁ | R₂ | Melting Point (°C.) | Elemental Analysis Theoretical (%) | | | Found (%) | | |
|---|---|---|---|---|---|---|---|---|---|---|
| | | | | | C | H | N | C | H | N |
| 8 | 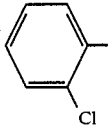 | H | OC₂H₅ | 45~46 | 67.59 | 5.67 | 9.85 | 67.39 | 5.39 | 9.87 |
| 9 | 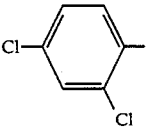 | Br | OH | 233~235 | 45.50 | 2.73 | 7.58 | 45.28 | 2.59 | 7.75 |
| 10 | 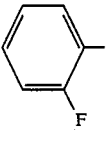 | Br | OH | 228~230 | 41.62 | 2.25 | 6.93 | 41.81 | 2.54 | 6.99 |
| 11 | 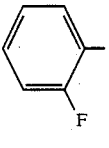 | Br | OH | 214~216 | 47.62 | 2.85 | 7.93 | 47.28 | 2.80 | 7.69 |
| 12 | 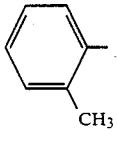 | H | OH | 225~227 | 61.31 | 4.04 | 10.21 | 61.52 | 3.98 | 10.43 |
| 13 | 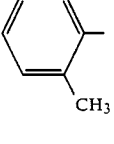 | Br | OH | 240~242 | 51.60 | 3.75 | 8.02 | 51.41 | 3.83 | 8.32 |
| 14 | 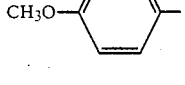 | H | OH | 218~219 | 66.66 | 5.22 | 10.36 | 66.91 | 5.08 | 10.21 |
| 15 | 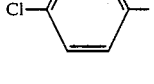 | H | OH | 222~224 | 62.93 | 4.93 | 9.79 | 63.11 | 4.72 | 9.89 |
| 16 | 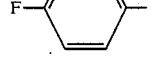 | Br | OH | 207~208 | 45.50 | 2.73 | 7.58 | 45.28 | 2.96 | 7.73 |
| 17 |  | Br | OH | 203~205 | 47.62 | 2.85 | 7.93 | 47.58 | 2.97 | 7.69 |

-continued $$\text{Ar—CO} \underset{N}{\overset{N}{\diagdown}} \overset{R_1}{\underset{COR_2}{\diagdown}}$$

| Example No. | Ar | $R_1$ | $R_2$ | Melting Point (°C.) | Theoretical (%) C | H | N | Found (%) C | H | N |
|---|---|---|---|---|---|---|---|---|---|---|
| 18 | CH₃—C₆H₄— | Br | OH | 190~192 | 51.60 | 3.75 | 8.02 | 51.47 | 3.83 | 8.31 |
| 19 | (CH₃)₂CH—C₆H₄— | Br | OH | 226~227 | 54.13 | 4.54 | 7.43 | 54.19 | 4.82 | 7.16 |
| 20 | 3,5-Cl₂-C₆H₃— | Br | OH | 204~207 | 41.62 | 2.25 | 6.93 | 41.57 | 2.48 | 6.77 |
| 21 | CH₃—C₆H₄— | H | OH | 217~218 | 66.66 | 5.22 | 10.36 | 66.84 | 5.20 | 10.24 |
| 22 | F—C₆H₄— | H | OH | 224~225 | 61.31 | 4.04 | 10.21 | 61.60 | 4.08 | 10.41 |
| 23 | 3,4-(CH₃)₂-C₆H₃— | Br | OH | 187~189 | 52.91 | 4.16 | 7.71 | 52.72 | 4.12 | 7.59 |
| 24 | (CH₃)₂CH—C₆H₄— | H | OH | 178~179 | 68.44 | 6.08 | 9.39 | 68.69 | 6.16 | 9.52 |
| 25 | 3,4-(CH₃)₂-C₆H₃— | H | OH | 200~201 | 67.59 | 5.67 | 9.85 | 67.83 | 5.39 | 9.74 |

ACTIONS OF THE COMPOUNDS OF THE PRESENT INVENTION

Methods for the pharmacological experiment of the compounds of the present invention and the pharmacological data obtained by the experiment, will be indicated hereunder.

EXPERIMENT 1

Inhibitory actions on the writhing induced by acetic acid in mice

Male ddY strain mice weighing 20-24 g were used a group consisting 7-9 animals. Each compound was orally administered to mice. Thirty minutes later, 0.6% acetic acid was abdominally administered at a dose of 0.1 ml/10 g. The number of writhing was counted 5 minutes after the administration of the acetic acid for 10 minutes. The inhibitory percentage were determined by comparing the number of writhing to the control group. The inhibitory percentage is shown in the following Table.

TABLE

| Test compound | Dose (mg/kg) | Inhibition (%) |
|---|---|---|
| Compound of Example 5 | 50 | 87.5 |
| Compound of Example 9 | 50 | 83.3 |
| Compound of Example 15 | 50 | 86.3 |
| Compound of Example 16 | 50 | 84.5 |
| Compound of Example 24 | 50 | 79.3 |

It has been found from the above results that compounds of the present invention have remarkable inhibiting actions on the writhing induced by acetic acid.

EXPERIMENT 2

Inhibitory actions on carrageenin-induced paw edema

Using male rats of Wistar strain each weighing approximately 150 g, 0.1 ml of 1% λ-carrageenin was subcutaneously injected into the paw of each rat to induce the reaction. Since then, the volume of paw edema was measured in time course. Each compound of the present invention was orally administered to the rats 60 minutes before the induction of the reaction. As shown in the following Table, the results were expressed in terms of inhibitory percentage in comparison with those in control group at 3 hours after the induction of the reaction.

TABLE

| Test compound | Dose (mg/kg) | Inhibition (%) |
|---|---|---|
| Compound of Example 5 | 50 | 48.4 |
| Compound of Example 9 | 50 | 50.1 |
| Compound of Example 15 | 50 | 53.9 |
| Compound of Example 16 | 50 | 50.7 |
| Compound of Example 24 | 50 | 51.6 |

It has been found from the above results that compounds of the present invention have significant inhibiting actions on carrageenin-induced paw edema.

EXPERIMENT 3

Gastric mucous damage test in rats

Using male rats of Wistar strain each weighing approximately 160 g, compounds of the present invention were orally administered to the rats previously fasting for 18 hours. Three point five hours later, 1 ml/rat of a 5% Pontamin Sky Blue solution was intravenously injected to the rats. Rats were dissected to remove the stomachs therefrom. A 10 ml of 70% ethanol was injected into the stomachs to fix them, and the stomachs were cut and washed with a 10% hydrogen peroxide/ethanol mixed liquid and then visually observed to fine whether ulcers were formed therein.

TABLE

| Test compound | Dose (mg/kg) | Ulcer formation (cases out of 6) |
|---|---|---|
| Compound of Example 5 | 100 | 0/6 |
| Compound of Example 9 | 100 | 0/6 |
| Compound of Example 15 | 100 | 0/6 |
| Compound of Example 16 | 100 | 0/6 |
| Compound of Example 24 | 100 | 0/6 |
| Aspirin | 100 | 6/6 |

TABLE-continued

| Test compound | Dose (mg/kg) | Ulcer formation (cases out of 6) |
|---|---|---|
| Indomethacine | 10 | 6/6 |

It has been found from the above results that compounds of the present invention will not cause gastric mucous membrane disturbances as side-effects when administered.

EXPERIMENT 4

Acute toxicity test in rats and mice

Each group consisting 8 animals such as male Wistar rats weighing about 120 g and male ddY mice weighing about 25 g was used. Compounds of the present invention were orally administered to the animals. General symptoms, changes in body weight and lethality of the test animals had been observed over a period of time for 14 days after the oral administration. The results are as shown in the following Table.

TABLE

| Test compound | $LD_{50}$ (mg/kg) Mouse(♂) | $LD_{50}$ (mg/kg) Rat(♂) |
|---|---|---|
| Compound of Example 5 | >3,000 | >5,000 |
| Compound of Example 9 | >3,000 | >5,000 |
| Compound of Example 15 | >3,000 | >5,000 |
| Compound of Example 16 | >3,000 | >5,000 |
| Compound of Example 24 | >3,000 | >5,000 |

It has been found from the above results that compounds of the present invention are remarkably low in toxicity.

EFFECTS OF THE INVENTION 3-aroyl-6,7-dihydro-5H-pyrrolo[1,2-c]imidazole-7-carboxylic acid derivatives of the present invention are those having a novel structure, which were first synthesized by the present inventors. As is clear from the foregoing Experiments, these compounds have conspicuous inhibiting actions on acetic acid-induced writhing and carrageenin-induced paw edema, and the like, with remarkably less side-effects on canal tracts and markedly less toxicity which has been found in tests for acute toxicity.

As has been so far described, the compounds of the present invention are excellent in medicinal efficacy, safety and the like and are very useful as anti-inflammatory and analgesic agents in the medicinal and pharmaceutical fields.

What is claimed is:

1. A 3-aroyl-6,7-dihydro-5H-pyrrolo imidazole-7-carboxylic acid derivative of formula

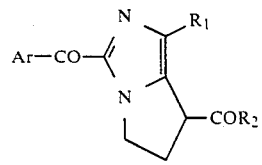

wherein $R_1$ is hydrogen or halogen; Ar is unsubstituted phenyl or phenyl substituted by 1 to 5 halogen atoms, alkyl groups or alkoxy groups; and $R_2$ is hydroxy, alkoxy or —NH—CH$_2$—COOH.

* * * * *